(12) United States Patent
Wood

(10) Patent No.: US 8,521,247 B2
(45) Date of Patent: Aug. 27, 2013

(54) CERTIFICATION APPARATUS AND METHOD FOR A MEDICAL DEVICE COMPUTER

(75) Inventor: Lockett E. Wood, Lyons, CO (US)

(73) Assignee: Covidien LP, Mansfield, MA (US)

( * ) Notice: Subject to any disclaimer, the term of this patent is extended or adjusted under 35 U.S.C. 154(b) by 425 days.

(21) Appl. No.: 12/980,971

(22) Filed: Dec. 29, 2010

(65) Prior Publication Data
US 2012/0172687 A1    Jul. 5, 2012

(51) Int. Cl.
*A61B 5/00*    (2006.01)
*G01D 18/00*    (2006.01)
*G21C 17/00*    (2006.01)

(52) U.S. Cl.
USPC ............ 600/323; 600/310; 702/104; 702/182

(58) Field of Classification Search
USPC ......... 600/310, 322, 323, 473, 476; 702/104, 702/182–186; 382/115; 703/21–22
See application file for complete search history.

(56) References Cited

U.S. PATENT DOCUMENTS

| | | | |
|---|---|---|---|
| 3,654,445 A | 4/1972 | Mikkelsen et al. | |
| 5,355,880 A | 10/1994 | Thomas et al. | |
| 5,416,582 A | 5/1995 | Knutson et al. | |
| 5,590,650 A | 1/1997 | Genova | |
| 5,630,413 A | 5/1997 | Thomas et al. | |
| 5,645,059 A | 7/1997 | Fein et al. | |
| 5,783,821 A | 7/1998 | Costello, Jr. | |
| 5,813,988 A | 9/1998 | Alfano et al. | |
| 5,818,583 A | 10/1998 | Sevick-Muraca et al. | |
| 5,835,617 A | 11/1998 | Ohta et al. | |
| 5,891,025 A | 4/1999 | Buschmann et al. | |
| 5,999,852 A | 12/1999 | Elabbady et al. | |
| 6,285,894 B1 | 9/2001 | Oppelt et al. | |
| 6,341,287 B1 | 1/2002 | Sziklai et al. | |
| 6,393,310 B1 | 5/2002 | Kuenstner | |
| 6,493,565 B1 | 12/2002 | Chance et al. | |
| RE37,970 E | 1/2003 | Costello | |
| 6,516,214 B1 | 2/2003 | Boas | |
| 6,549,284 B1 | 4/2003 | Boas | |
| 6,571,188 B1 * | 5/2003 | Clarridge et al. | ............. 702/104 |

(Continued)

FOREIGN PATENT DOCUMENTS

| | | |
|---|---|---|
| AU | 732799 B2 | 5/2001 |
| EP | 734221 | 7/1998 |

(Continued)

OTHER PUBLICATIONS

U.S. Food and Drug Administration—Guidance for Industry, FDA Reviewers and Compliance on Off-The-Shelf Software Use in Medical Devices (Sep. 9, 1999).

*Primary Examiner* — Eric Winakur
*Assistant Examiner* — Chu Chuan (JJ) Liu

(57) ABSTRACT

Provided herein are methods and apparatuses for certifying computers for use in conjunction with medical devices. These methods may be used in conjunction with a computer that includes software for operating the medical device. To certify a particular computer, one or more testing algorithms or routines for processing data, e.g., data representative of a typical output generated by use of the medical device on a patient, may be executed and the results may be compared to an expected result. In particular embodiments, the certification process may use data stored on the device itself to determine certification or may use data stored with or bundled with the software for operating the device.

15 Claims, 4 Drawing Sheets

(56) References Cited

U.S. PATENT DOCUMENTS

| | | |
|---|---|---|
| 6,577,884 B1 | 6/2003 | Boas |
| 6,587,703 B2 | 7/2003 | Cheng |
| 6,597,931 B1 | 7/2003 | Cheng |
| 6,631,281 B1 | 10/2003 | Kastle |
| 6,658,277 B2 | 12/2003 | Wasserman |
| 6,662,128 B2 | 12/2003 | Barbour et al. |
| 6,681,198 B2 | 1/2004 | Buote |
| 6,708,049 B1 * | 3/2004 | Berson et al. .................. 600/323 |
| 6,748,259 B1 | 6/2004 | Benaron et al. |
| 6,829,496 B2 | 12/2004 | Nagai et al. |
| 6,862,091 B2 | 3/2005 | Johnson |
| 6,901,154 B2 * | 5/2005 | Dunn ........................... 382/115 |
| 6,918,878 B2 | 7/2005 | Brodnick |
| 6,931,269 B2 | 8/2005 | Terry |
| 6,957,094 B2 | 10/2005 | Chance et al. |
| 6,993,371 B2 | 1/2006 | Kiani et al. |
| 7,027,850 B2 | 4/2006 | Wasserman |
| 7,043,293 B1 | 5/2006 | Baura |
| 7,047,055 B2 | 5/2006 | Boas |
| 7,054,453 B2 | 5/2006 | Causevic et al. |
| 7,054,454 B2 | 5/2006 | Causevic et al. |
| 7,060,035 B2 | 6/2006 | Wasserman |
| 7,072,705 B2 | 7/2006 | Miga et al. |
| 7,090,648 B2 | 8/2006 | Sackner |
| RE39,268 E | 9/2006 | Merrick et al. |
| 7,187,441 B1 | 3/2007 | Sevick-Muraca et al. |
| 7,203,267 B2 | 4/2007 | De Man et al. |
| 7,212,128 B2 | 5/2007 | Schenker |
| 7,218,959 B2 | 5/2007 | Alfano et al. |
| 7,220,220 B2 | 5/2007 | Stubbs et al. |
| 7,225,013 B2 | 5/2007 | Geva et al. |
| 7,277,741 B2 | 10/2007 | Debreczeny et al. |
| 7,349,726 B2 | 3/2008 | Casciani et al. |
| 7,349,731 B2 | 3/2008 | Jiang |
| 7,376,454 B2 | 5/2008 | Casciani et al. |
| 7,398,115 B2 | 7/2008 | Lynn |
| 7,415,298 B2 | 8/2008 | Casciani et al. |
| 7,428,432 B2 | 9/2008 | Ali et al. |
| 2002/0082489 A1 | 6/2002 | Casciani et al. |
| 2002/0190863 A1 | 12/2002 | Lynn |
| 2004/0010188 A1 | 1/2004 | Wasserman |
| 2004/0087846 A1 | 5/2004 | Wasserman |
| 2004/0147823 A1 | 7/2004 | Kiani et al. |
| 2004/0254481 A1 | 12/2004 | Brodnick |
| 2005/0049470 A1 | 3/2005 | Terry |
| 2005/0065417 A1 | 3/2005 | Ali et al. |
| 2005/0066969 A1 | 3/2005 | Rick |
| 2005/0175540 A1 | 8/2005 | Oraevsky et al. |
| 2005/0222502 A1 | 10/2005 | Cooper |
| 2005/0247311 A1 | 11/2005 | Vacchiano et al. |
| 2005/0251344 A1 | 11/2005 | Appel et al. |
| 2005/0277818 A1 | 12/2005 | Myers |
| 2006/0111749 A1 | 5/2006 | Westenskow et al. |
| 2006/0185669 A1 | 8/2006 | Bassovitch |
| 2006/0195026 A1 | 8/2006 | Casciani et al. |
| 2006/0195027 A1 | 8/2006 | Casciani et al. |
| 2006/0206019 A1 | 9/2006 | Zhang et al. |
| 2006/0211929 A1 | 9/2006 | Casciani et al. |
| 2006/0258926 A1 | 11/2006 | Ali et al. |
| 2007/0016096 A1 | 1/2007 | Mcnabb |
| 2007/0062531 A1 | 3/2007 | Fisher et al. |
| 2007/0118045 A1 | 5/2007 | Naghavi et al. |
| 2007/0172392 A1 | 7/2007 | Sen et al. |
| 2007/0181128 A1 | 8/2007 | Stroetz et al. |
| 2007/0208233 A1 | 9/2007 | Kovacs |
| 2007/0208262 A1 | 9/2007 | Kovacs |
| 2007/0221225 A1 | 9/2007 | Kutt |
| 2007/0282478 A1 | 12/2007 | Al-Ali et al. |
| 2008/0030468 A1 | 2/2008 | Ali et al. |
| 2008/0039701 A1 | 2/2008 | Ali et al. |
| 2008/0045832 A1 | 2/2008 | Mcgrath |
| 2008/0059249 A1 | 3/2008 | Joao |
| 2008/0059250 A1 | 3/2008 | Joao |
| 2008/0081963 A1 | 4/2008 | Naghavi et al. |
| 2008/0081974 A1 | 4/2008 | Pav |
| 2008/0091089 A1 | 4/2008 | Guillory et al. |
| 2008/0091090 A1 | 4/2008 | Guillory et al. |
| 2008/0097173 A1 | 4/2008 | Soyemi et al. |
| 2008/0146895 A1 | 6/2008 | Olson et al. |
| 2008/0177160 A1 | 7/2008 | Al Ali et al. |
| 2008/0208019 A1 | 8/2008 | Nitzan |
| 2008/0287756 A1 | 11/2008 | Lynn |

FOREIGN PATENT DOCUMENTS

| | | |
|---|---|---|
| EP | 1721629 | 11/2006 |
| EP | 1986543 | 11/2008 |
| WO | WO9313706 A2 | 7/1993 |
| WO | WO9512349 A1 | 5/1995 |
| WO | WO9516387 | 6/1995 |
| WO | WO9526676 | 10/1995 |
| WO | WO0117421 | 3/2001 |
| WO | WO2007097702 | 8/2007 |

* cited by examiner

US 8,521,247 B2

CERTIFICATION APPARATUS AND METHOD FOR A MEDICAL DEVICE COMPUTER

BACKGROUND

The present disclosure relates generally to medical monitors and, more particularly, to certification of computers that are used in conjunction with medical devices.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of healthcare, caregivers (e.g., doctors and other healthcare professionals) often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

Monitoring devices are often configured as dedicated monitoring units (e.g., a stand-alone pulse oximetry monitor) with integral processing circuitry for receiving measurements from medical devices and converting these measurements into medical information that is meaningful to a clinician. However, certain types of medical devices are capable of being used with configurable personal computers that are loaded with software that communicates with the medical device. For example, a medical sensor may be capable of communicating directly with a personal computer, which, with the appropriate software, is able to receive the sensor measurements and process and display information related to the sensed data. In this manner, an off-the shelf computer may act as a medical monitor.

In contrast to dedicated monitoring devices, which are limited-purpose machines, a personal computer (e.g., a general purpose computer) may be used for a variety of tasks and, as such, may run a variety of different software programs. Different end users may select different brands and/or computer models depending on their own needs. Accordingly, different types of computers may have differing levels of compatibility with particular medical devices. Further, an individual computer may be frequently upgraded or changed from its factory condition according to the needs of the user, and these updates often occur automatically in response software or operating system changes. In certain instances, these changes may cause certain incompatibilities with installed software for receiving medical device information.

BRIEF DESCRIPTION OF THE DRAWINGS

Advantages of the disclosed techniques may become apparent upon reading the following detailed description and upon reference to the drawings in which.

DETAILED DESCRIPTION

Figure 1:
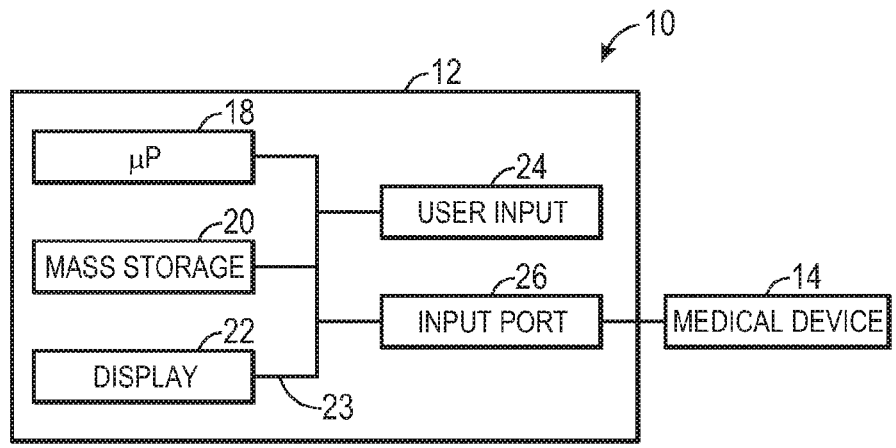
FIG. 1 illustrates a block diagram of a certification system for a computer to be used in conjunction with a medical device, in accordance with an embodiment of the present technique.

One or more embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Medical monitors are built according to FDA or other regulatory specifications and undergo quality testing by the manufacturer. However, in the case of medical devices that may be used with personal or off-the-shelf computers, while the medical devices themselves are subjected to quality testing by the manufacturer, the computers may be purchased by an end user and, thus, are not necessarily tested by the medical device manufacturer for compatibility with the medical device. In such cases, a particular model of computer may be certified by a technician as being compatible with a particular type of medical device and the device's associated software for processing data or measurements. This certification may involve having a technician run diagnostic tests on an individual model of a computer to verify that the device and installed software are compatible and that accurate readings and data processing are performed. Such certifications are time-consuming and involve skilled personnel. In addition, the certification must be repeated for different brands and different models of computers. Because computer vendors frequently change their offerings as technology changes and improves, a particular computer model that has been certified for use with a particular medical device may become obsolete and no longer available on the market. In addition, end users may change the functionality of their own computers, which may introduce device incompatibilities.

Provided herein is an automatic certification technique for a computer configured to be used in conjunction with a medical device. In addition, provided herein are systems and computers that include certification functionality (e.g., a certification module). The certification may involve using the computer to process stored data representative of data collected by the medical device and comparing the processed results to an expected result. In this manner, the computer may be certified as performing according to expectations. In certain embodiments, the certification module as well as the data representative of the medical device may be installed directly on the computer (e.g., bundled with software for receiving and processing the medical device signal) so that the certification may take place without any outside input from the medical device. In other embodiments, an input from an associated device may trigger the certification process.

It should be understood that the certification techniques may be used in conjunction with medical devices for diagnosis and/or therapy. Such devices may include devices for sensing physiological parameters, collecting medical data (e.g., imaging data), delivering therapy, and performing procedures. The devices may include blood or tissue constituent sensors (e.g., pulse oximetry sensors, carbon dioxide sensors, or aquametry sensors), patient temperature sensors, transvascular fluid exchange sensors, blood flow, cardiovascular effort, glucose levels, total hematocrit, electrocardiography, electroencephalograpy, airway products and ventilation devices, infusion pumps, blood pressure devices, apnea masks, ultrasound transducers, and cardiac defibrillators. In addition, the certification techniques may be used with computers having installed software for receiving and processing signals from a medical device to generate medical information. Such computers may include personal computers, off-the-shelf computers, multi-purpose computers, laptops, desktop computers, notebooks, mobile communication devices, or any suitable computing device.

Turning now to the figures, FIG. 1 depicts an embodiment of a computer certification system 10 that includes a computer 12 configured to be used on conjunction with a medical device 14. The computer 12 includes a processor 18 for executing routines or instructions stored in mass storage 20, such as instructions for implementing the techniques discussed herein and instructions associated with medical device operating software. Additionally, the computer 12 may include a display 22 coupled to the processor 18 via internal bus 23 and configured to display information regarding the output generated by the medical device, such as physiological parameters and/or alarm or operating indications. In certain embodiments, the computer 12 is a multi-purpose computer that is configured to run any number of software programs, such as word processing, database programs, and internet access. While installation of the medical device operating software may disable or prevent operation of particular types of programs, other maintenance programs may be configured to operate in the background. As such, the display 22 may also be used for display of other information, e.g., in addition to medical device information, according to the inputs provided by the user, and the computer 12 may include various input components 24, such as knobs, switches, keys and keypads, buttons, etc., to provide for operation and configuration of the computer 12. The computer 12 may also include an input port 26 for coupling to the medical device 14. For example, the computer may include a USB port for coupling to an external device. In other embodiments, the computer 12 may include a transceiver for coupling to wireless medical devices.

Figure 2:
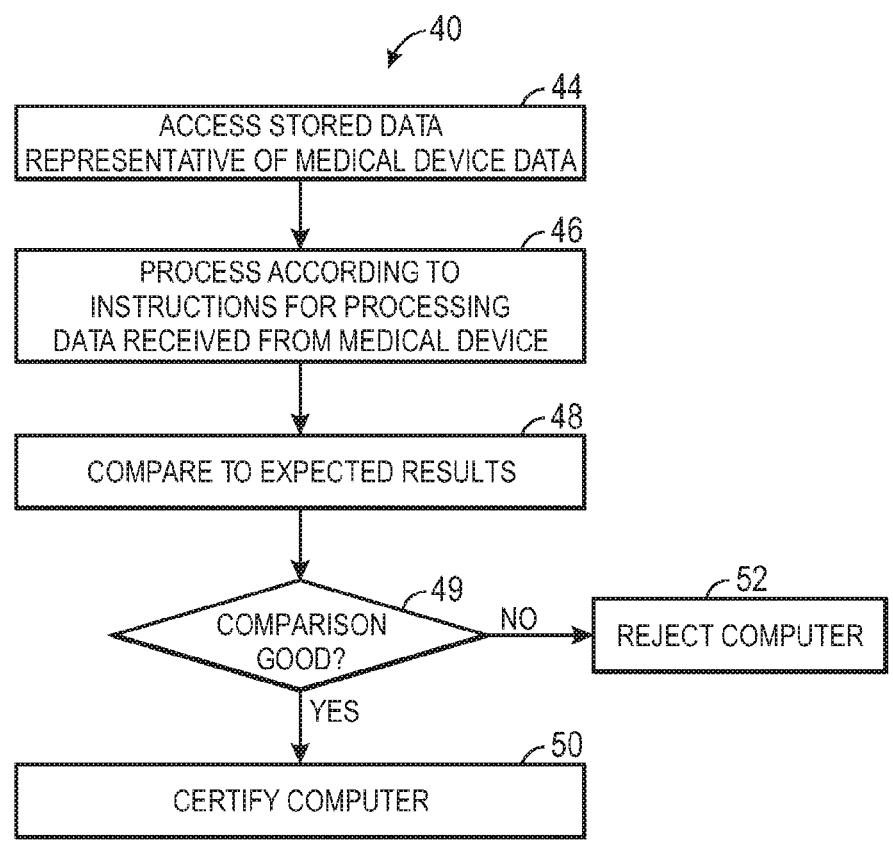
FIG. 2 illustrates a flow diagram of a certification method in accordance with an embodiment of the present technique.

FIG. 2 is a process flow diagram illustrating a method 40 for certifying the computer 12. The method may be performed as an automated procedure by a system, such as a system 10 that includes the computer 12 and the medical device 14, or by the computer 12 without an associated medical device 14. In addition, certain steps of the method may be performed by a processor, e.g., processor 18, that executes stored instructions for implementing certain steps of the method 40.

According to a particular embodiment, instructions for certification stored on the computer 12 access stored data that is representative of data generated by the medical device 14 at step 44. It is envisioned that, in the depicted embodiment, the stored data may be stored in computer memory 20 or a portable memory device (e.g., a flash memory device). Accordingly, the stored data may be accessed when the computer 12 is not coupled to the medical device 14. The certification instructions may be part of medical device software for receiving signals from the medical device 14 and generating medical information. In particular implementations, installation of the medical device software is accompanied by executing the method 40 to complete the installation. For example, the installation and/or certification may be performed by an end user. In other embodiments, the installation and certification may be performed by a vendor of the software and medical device. The vendor may purchase an off-the-shelf computer, install the software, and initiate the steps of the method 40 to certify the computer 12. In other embodiments, the certification process 40 may begin upon computer startup or when the medical device software is accessed. That is, regardless of whether the initial certification was initiated by a vendor or the end user, additional certifications may be completed during the operation of the computer 12.

At step 46, the stored data is processed according to the instructions installed on the computer 12 for processing incoming signals from the medical device 14. The processed output of the medical device operating software is compared to an expected result at step 48. At decision step 49, if the processed output is within an acceptable deviation from the expected result, the method 40 proceeds to step 50, and the computer is certified to be used with the medical device 14. If the processed output is outside of an acceptable deviation from the expected result, the method 40 proceeds to step 52, and the computer is not certified or is rejected. Optionally, the method 40 may prevent incoming signals from the medical device 14 and/or coupling of the medical device 14 to the computer 12 if the computer 12 is rejected. In other embodiments, the medical device software may be prevented from completing installation if the computer 12 is rejected.

The stored data is representative of a typical medical device output when the medical device 14 is in operation (e.g., coupled to a patient). In particular embodiments, the stored data may be historical data that has been collected (e.g., recorded or stored) from a test device and that provides sufficient information for generating medical information about a patient. A test device may be a version of the medical device 14 that has been verified to generate a representative signal for a particular physiological parameter or other medical data. In other embodiments, the stored data may be simulated data that simulates the incoming signal of the medical device 14. By using data from a test device or simulated data, the certification process may provide information about the functionality of the computer 12 and its installed software that is isolated from any variations or irregularities in a particular medical device 14. That is, because the stored data is not generated by the medical device 14 itself, the certification may be specific to the computer 12. In other implementations, it may be advantageous to provide stored data that has been collected by the medical device 14 in question. For example, if the medical device 14 has been customized for a particular end use, the stored data may be generated from the medical device 14 for use in certification.

In certain embodiments, the medical device 14 may be configured to generate an analog signal or a digital signal that is further processed via hardware and/or software to condition the signal and generate an output representative of medical information. For example, if the medical device 14 is a temperature sensor, the stored data representative of the medical device signal may be stored in the form of an analog signal in which the voltage varies according to the sensed temperature. In other embodiments, the data representative of an analog signal may be converted to a digital signal, and the certification process may include a digital-to-analog conversion step. The analog signal or digital signal may be processed according to instructions encoded in the installed software, which may include correlating particular voltages to particular temperature readings and providing an indication of the sensed temperatures. The calculated temperatures may be compared to the expected results, e.g., results from a test run or results that were independently confirmed, to determine if the computer 12 is compatible with the medical device 14. If the calculated temperatures deviate from the expected temperatures by less than a predetermined amount (e.g., less than a standard deviation), the computer 12 may be certified.

Certification or rejection of the computer 12 may trigger one or more audible or visual indicators. For example, the display of an indicator or text message may be triggered upon certification of the computer 12. The indicator may be a green light, a check mark, and/or a message that refers to successful certification. Rejection of the computer 12 (e.g., a failure to be certified) may trigger an alarm, a red light, a message related to unsuccessful certification, and/or an inability to open or access the medical device software.

Figure 3:
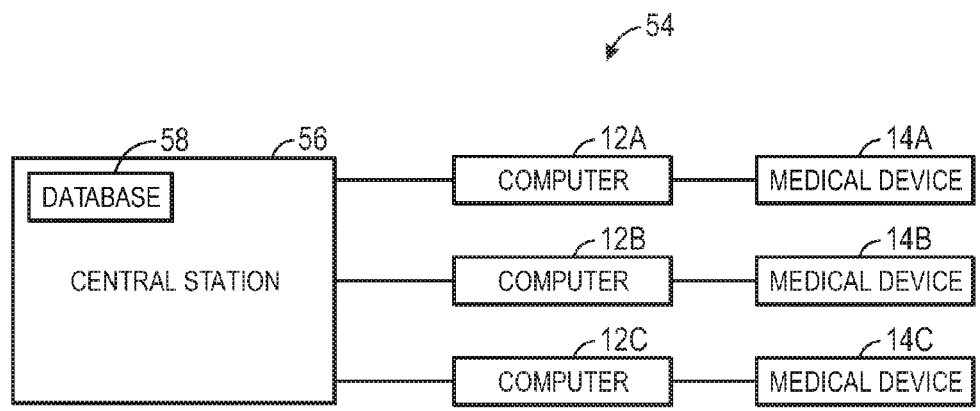
FIG. 3 illustrates a perspective view of a central certification system for a medical facility.

The certification information may be provided to a regulatory agency, such as the Food and Drug Administration (FDA), as part of the certification process. Computer certification, such as certification via method 40, may be provided as part of the guidelines for approval of the medical device 14. In addition, all or part of a certification process may form part of text-based instructions or other training materials for the medical device 14. The device manufacturer may designate particular computer hardware specifications, including processor specifications, (manufacturer, speed, and features), RAM (memory size), hard disk size, other storage, communications, display, etc., and software specifications, such as operating system, drivers, utilities, etc as being compatible with the medical device software in question. These specifications may be provided as part of a software requirements specifications (SRS) document. As part of this or other submitted documentation for approval, the device manufacturer may specify how the use of the medical device software by an end user may be regulated or monitored, including any certification of the computer 12 to be used with the medical device 14. For example, the specifications may include guidelines for the frequency of the certification, such as every time the computer 12 is booted or after every update to the computer 12. In one embodiment, installation of new software or computer updates will trigger certification, such as via method 40, either automatically or through a pop-up window or reminder on the computer display Certification information for the computer 12 may be automatically provided to the FDA, or may be stored in the computer's memory 20 for later review or submission. FIG. 3 illustrates a block diagram of a system 54 for assembling certification information. The system 54 includes a central station 56 completion of certification of the computer 12 may be accompanied by entry of the certification date, time, or other information in a log file or database 58. The database 58 may compile certification information from several computers (e.g., computers 12a, 12b, and 12c) that are configured to couple to medical devices (e.g., medical devices 14a, 14b, and 14c). The central station 56 may store certification information to be accessed during an audit or review of a medical facility.

Figure 4:
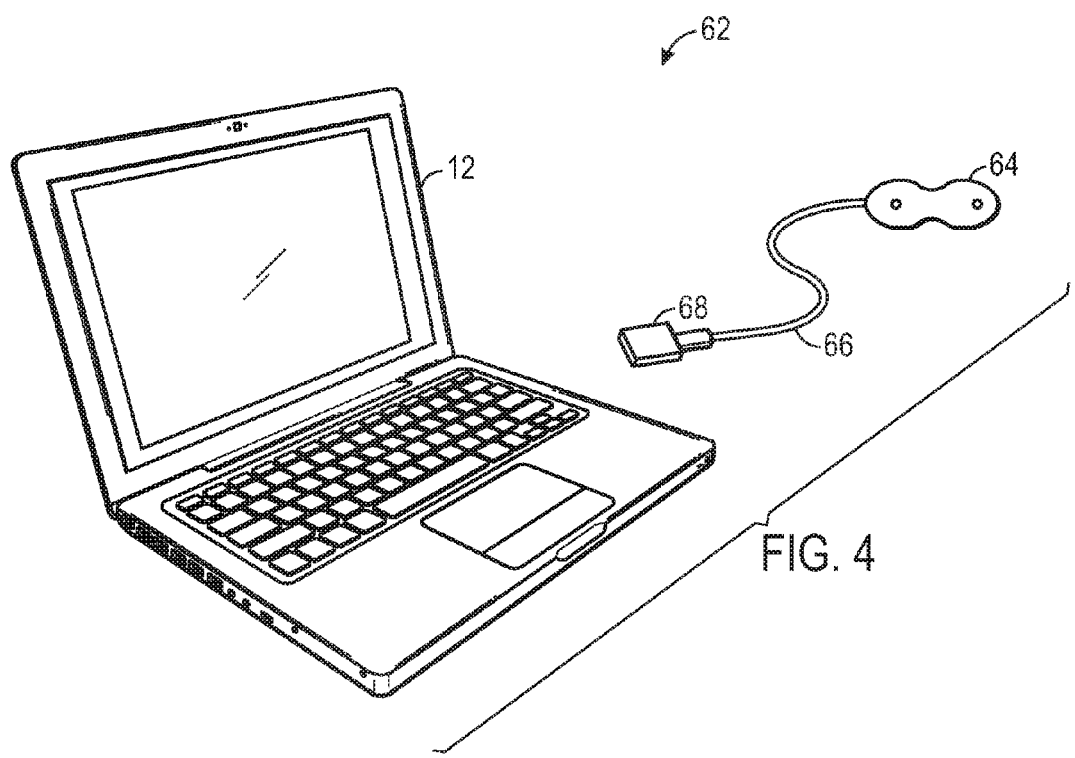
FIG. 4 illustrates a perspective view of a certification system to be used in conjunction with a medical sensor.

In a specific embodiment, the certification techniques may be used in conjunction with a pulse oximetry system. FIG. 4 is a perspective view of a pulse oximetry system 62 with the computer 12 that may couple to a pulse oximetry sensor 64. The sensor 64 may include optical components such as a light emitter (e.g., a light emitting diode) and a light detector (e.g., a photodetector) that are applied to a patient and may be used to generate a plethysmographic waveform, which may be further processed by the computer 12. The sensor 64 may be coupled to the computer 12 wirelessly, or via a cable 66 that terminates in a connector 68 that is configured to couple to the computer. In a specific embodiment, the sensor 64 may be pulse oximetry sensor available from Nellcor-Puritan Bennett LLC, including a clip-type sensor suitable for placement on an appendage of a patient, e.g., a digit, an ear, etc. In other embodiments, the sensor 64 may be a bandage-type sensor having a generally flexible sensor body to enable conformable application of the sensor to a sensor site on a patient. In yet other embodiments, the sensor 64 may be secured to a patient via adhesive (e.g., in an embodiment having an electrode sensor) on the underside of the sensor body or by an external device, such as headband or other elastic tension device. In yet other embodiments, the sensor 64 may be configurable sensors capable of being configured or modified for placement at different sites (e.g., multiple tissue sites, such as a digit, a forehead of a patient, etc.). In embodiments in which the sensor 64 is wireless, wireless communication with the computer 12 may be accomplished using any suitable wireless standard, such as the ZigBee standard, WirelessHART standard, Bluetooth standard, IEEE 802.11x standards, or MiWi standard.

Figure 5:
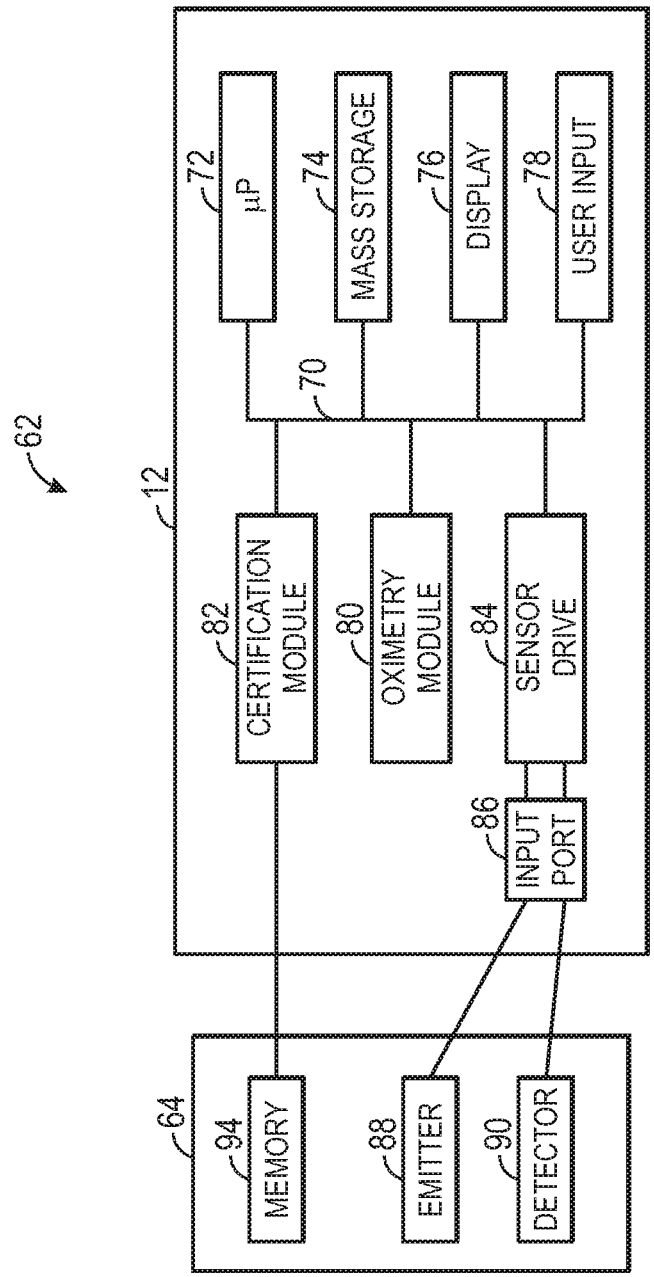
FIG. 5 illustrates a block diagram of a certification system, in accordance with an embodiment of the present technique.

FIG. 5 is a block diagram of the system 62. The computer 12 includes microprocessor 70 coupled to an internal bus 72. Also connected to the bus 72 may be a mass storage device 74, a display 76, and a user input 78. As depicted, the computer 12 may include functional modules, such as an oximetry module 80 and a certification module 82. In other embodiments, the functionality of the oximetry module 80 and certification module 82 may be achieved via the microprocessor 70 executing routines stored in the mass storage device 74. In addition, the computer 12 includes a sensor drive 84 coupled to a sensor input port 86.

The sensor drive 84 may include a time processing unit (TPU) to provide timing control signals to light drive circuitry, which controls when the optical components of the sensor 64, such as light emitter 88 and light detector 90, are activated, and, if multiple light sources are used, the multiplexed timing for the different light sources. The sensor drive 84 may also control the gating-in of signals from sensor 64 through one or more switching circuits. The received signal from the pulse oximetry sensor 64 may be passed to the oximetry module 80, which may include one or more signal conditioning elements that may be hardware or software-enabled, including an amplifier, a low pass filter, and an analog-to-digital converter. Based at least in part upon the received signals, the oximetry module 80 may calculate the oxygen saturation and/or heart rate using various algorithms, such as those employed by the Nellcor™ N-600x™ pulse oximetry monitor, which may be used in conjunction with various Nellcor™ pulse oximetry sensors, such as OxiMax™ sensors. These algorithms may employ certain coefficients, which may be empirically determined, and may correspond to the wavelengths of light used. In one embodiment, the correction coefficients may be provided as a lookup table.

In the depicted embodiment, a memory element 94 associated with the sensor 64 is configured to store certain information that is accessed by the certification module 82, such as stored data representative of output by the detector 90. The memory element 94 may also store calibration and identification information, including compatibility information for the computer 12. For example, the memory element 94 may store compatible medical device software version information that may be accessed by the calibration module 82 as part of the certification process. The memory element 94 may be associated with the sensor body, the cable 66, or the connector 68. In other embodiments, data representative of detector output may be stored on the computer 12 as part of the certification module 82.

Figure 6:
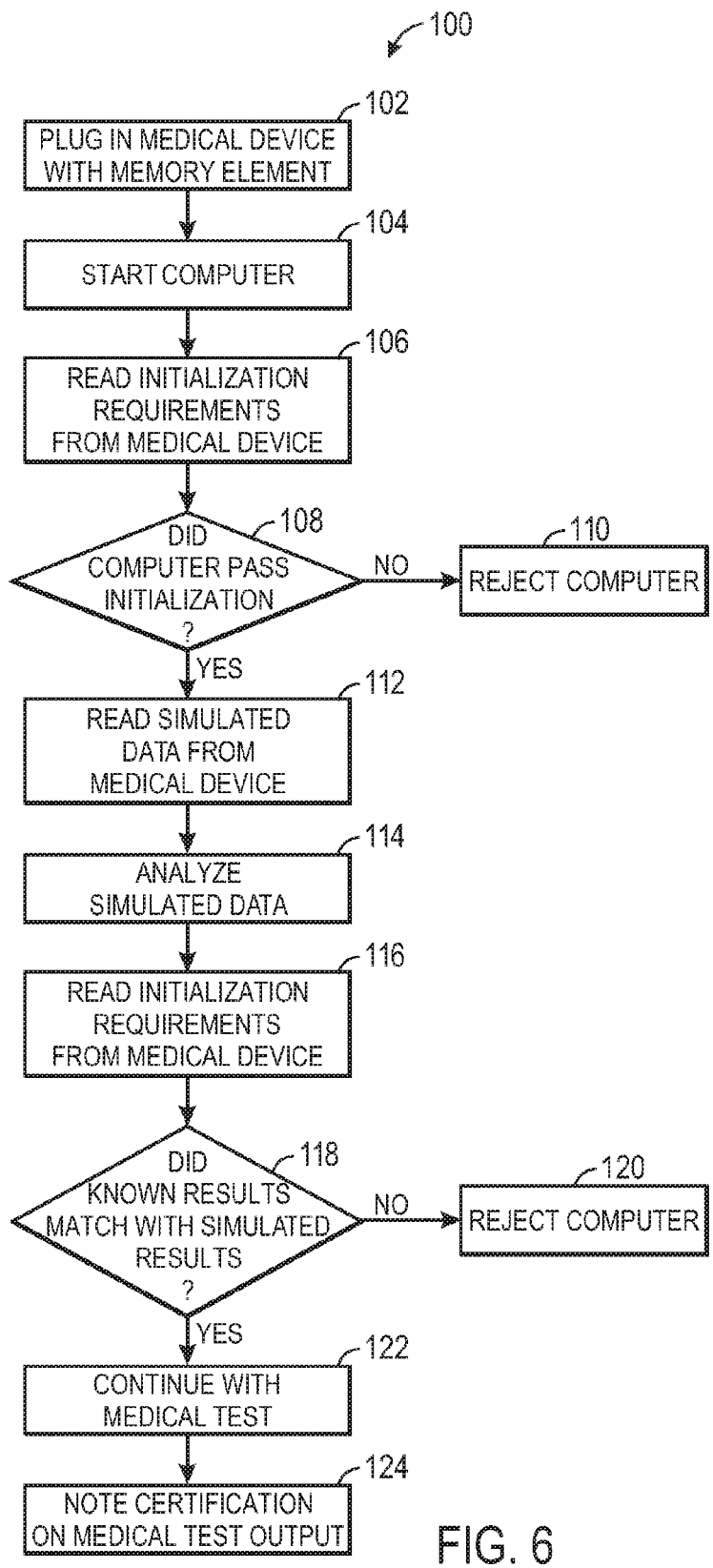
FIG. 6 illustrates a flow diagram of a certification method in accordance with an embodiment of the present technique.

The computer 12 is capable of reading the information from the memory element 94 to as part of the certification process. FIG. 6 is a process flow diagram illustrating a method 100 for certifying the computer 12 in conjunction with the sensor 64, on which data representative of sensor data is stored. According to an embodiment, the method 100 begins at step 102 by coupling the pulse oximetry sensor 64 to the computer 12 and starting the computer 12 (e.g., booting the computer or opening the medical device software installed on the computer) at step 104.

The computer 12 reads the initialization requirements based on information stored in the memory element 94 at step 106 to determine if the computer 12 passes an initialization test at step 108. The initialization requirements may include software and sensor compatibility requirements (e.g., if the sensor is from a manufacturer that is supported by the software), software and hardware specifications, and software version specifications. The stored information may include explicit initialization information, or may include identification information for the sensor that may be further analyzed by the certification module 82 to determine compatibility. If the computer 12 is not compatible with the medical device (e.g., sensor 64), the computer 12 is rejected at step 110. If the computer 12 passes the initialization requirements, the method 100 moves to step 112 to read simulated data stored on the memory element 94. The simulated data may be processed by the oximetry module 80 at step 114 and the results compared with expected results at step 116. If the results do not match, the computer is rejected at step 120. If the results match expected results, the computer 12 is certified and the software may continue operating at step 122. An indication of successful certification may be provided at step 124.

The embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A computer, comprising:
   a processor configured to be coupled to a medical device, wherein the processor is configured to execute routines for:
   receiving an input representative of a medical device measurement data;
   generating simulated medical information from the input;
   comparing the simulated medical information to an expected result; and
   determining a certification of the computer to generate medical information from the medical device based on the comparison.

2. The computer of claim 1, comprising stopping or exiting routines for processing a signal from the medical device if the simulated medical information deviates from the expected result.

3. The computer of claim 1, comprising displaying an indication related to the certification on a display.

4. The computer of claim 1, comprising accessing the input representative of the medical device from a memory associated with a medical sensor.

5. The computer of claim 1, comprising accessing the input representative of the medical device from a portable mass storage device.

6. The computer of claim 1, comprising accessing the input representative of the medical device from a memory of the computer.

7. The computer of claim 1, comprising providing information related to the certification to a regulatory agency.

8. The computer of claim 1, wherein the medical device comprises a pulse oximetry sensor.

9. The computer of claim 8, wherein the simulated medical device information comprises a plethysmographic waveform, a heart rate, or an oxygen saturation value.

10. A method, comprising:
    using a computer to:
    access a memory element associated with a medical device, wherein the memory element comprises stored information representative of a measurement data output of the medical device;
    generate simulated medical information from the stored information;
    compare the simulated medical information to an expected result; and
    determine a certification of the computer to generate medical information from the medical device based on the comparison.

11. The method of claim 10, wherein the memory element further comprises stored specification requirements.

12. The method of claim 11, further comprising using the computer to compare the specification requirements to specifications of the computer.

13. The method of claim 12, comprising using the computer to generate an output that the computer is not compatible with the medical device if the specification requirements do not match the specifications of the computer.

14. The method of claim 10, comprising using the computer to generate an output that the computer is not compatible with the medical device if the simulated medical information deviates from the expected result.

15. The method of claim 10, comprising using the computer to prevent generating medical information from the medical device if the simulated medical information deviates from the expected result.

* * * * *